United States Patent [19]
Yarus et al.

[11] Patent Number: 5,871,924
[45] Date of Patent: Feb. 16, 1999

[54] METHOD FOR THE PRODUCTION OF LIGANDS CAPABLE OF FACILITATING AMINOACYL-RNA SYNTHESIS

[75] Inventors: Michael Yarus; Mali Illangasekare, both of Boulder, Colo.

[73] Assignee: NeXstar Pharmaceuticals, Inc., Boulder, Colo.

[21] Appl. No.: 787,042

[22] Filed: Jan. 27, 1997

[51] Int. Cl.⁶ .............................. C12Q 1/68; C12P 19/34; C07H 21/04

[52] U.S. Cl. ........................... 435/6; 435/91.1; 435/91.2; 435/91.51; 536/22.1

[58] Field of Search ............................ 435/6, 91.2, 91.1, 435/91.51; 536/22.1

[56] References Cited

U.S. PATENT DOCUMENTS 5,270,163 12/1993 Gold et al. ................................. 435/6

FOREIGN PATENT DOCUMENTS

| | | |
|---|---|---|
| 2 183 661 | 6/1985 | United Kingdom . |
| WO 89/06694 | 7/1989 | WIPO . |
| WO 92/14843 | 9/1992 | WIPO . |
| WO 96/06944 | 3/1996 | WIPO . |
| WO 96/40723 | 12/1996 | WIPO . |

OTHER PUBLICATIONS

Bartel and Szostak (1993) Science 261:1411.
Beaudry and Joyce (1992) Science 257:635.
Cech (1987) Science 236:1532.
Dai et al. (1995) Science 267:237.
Ellington and Szostak (1990) Abstracts of papers presented at the 1990 meeting on RNA Processing, Cold Spring Harbor Laboratory, Cold Spring Harbor, NY, p. 84.
Joyce (1989) Gene 82:83.
Joyce and Inoue (1989) Nucleic Acids Research 17:711.
Kinzler and Vogelstein (1989) Nucleic Acids Research 17:3645.
Kramer et al. (1974) J. Mol. Biol. 89:719.
Levisohn and Spiegelman (1968) Proc. Nat'l. Acad. Sci. USA 60:866.
Levisohn and Spiegelman (1969) Proc. Nat'l. Acad. Sci. USA 63:805.
Lorsch and Szostak (1994) Nature 371:31.
McCorkle and Altman (1987) Journal of Chemical Education 64:221.
Oliphant et al. (1986) Gene 44:177.
Oliphant and Struhl (1987) Methods in Enzymology 155:568.
Oliphant et al. (1989) Mol. Cell. Biol. 9:2944.
Oliphant and Struhl (1988) Nucleic Acids Research 16:7673.
Pan and Uhlenbeck (1992) Biochemistry 31:3887.
Piccirilli et al. (1992) Science 256:1420.
Prudent et al. (1994) Science 264:1924.
Robertson and Joyce (1990) Nature 344:467.
Schimmel (1989) Cell 58:9.
Thiesen and Bach (1990) Nucleic Acids Research 18:3203.
Tuerk and Gold (1990) Science 249:505.
Illangasekare et al. Aminoacyl–RNA Synthesis Catalyzed by an RNA. Science, vol. 267, pp. 643–647.

*Primary Examiner*—Stephanie W. Zitomer
*Assistant Examiner*—Joyce Tung
*Attorney, Agent, or Firm*—Swanson & Bratschun LLC

[57] ABSTRACT

The instant invention provides a method for identifying and preparing nucleic acid ligands capable of facilitating aminoacyl-RNA synthesis. The nucleic acid ligands are identified and produced by exposure of candidate nucleic acid sequences to a reactant under conditions conducive to reaction, wherein nucleic acid sequences having facilitative activity are able to facilitate or enhance a reaction between the reactant molecule and nucleic acid sequence. Included in the invention are specific RNA ligands capable of facilitating aminoacyl-RNA synthesis identified by the SELEX method.

16 Claims, 4 Drawing Sheets

Figure 4

METHOD FOR THE PRODUCTION OF LIGANDS CAPABLE OF FACILITATING AMINOACYL-RNA SYNTHESIS

This work was partially supported by grants from the United States Government through the National Institute of Health (NIH research grants GM30881 and GM48080). The United States Government may have certain rights in this invention.

This is a prov. appln. of 60/011095, filed Feb. 2, 1996.

FIELD OF THE INVENTION

The present invention relates to the field of nucleic acid chemistry. Specifically, this invention describes a method for identifying and preparing nucleic acid ligands which facilitate aminoacyl-RNA synthesis. The method utilized herein for identifying such RNA ligands is a variation of the SELEX process, an acronym for Systematic Evolution of Ligands by EXponential Enrichment. This invention includes RNA ligands which facilitate aminoacyl-RNA synthesis.

BACKGROUND OF THE INVENTION

A method for the in vitro evolution of nucleic acid molecules with highly specific binding to target molecules has been developed. This method, Systematic Evolution of Ligands by EXponential enrichment, termed the SELEX process, is described in U.S. patent application Ser. No. 07/536,428, filed Jun. 11, 1990, entitled "Systematic Evolution of Ligands by EXponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled "Methods for Identifying Nucleic Acid Ligands," now U.S. Pat. No. 5,270,163 (see also WO 91/19813), each of which is herein specifically incorporated by reference. Each of these applications, collectively referred to herein as the SELEX Patent Applications, describes a fundamentally novel method for making a nucleic acid ligand to any desired target molecule. The SELEX process provides a class of products which are referred to as nucleic acid ligands, such ligands having a unique sequence, and which have the property of binding specifically to a desired target compound or molecule. Each SELEX-identified nucleic acid ligand is a specific ligand of a given target compound or molecule. SELEX is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The dogma for many years was that nucleic acids had primarily an informational role. Through the application of SELEX, it has become clear to the present inventors that nucleic acids have three dimensional structural diversity not unlike proteins. As such, the present inventors have recognized that SELEX or SELEX-like processes could be used to identify nucleic acids which can facilitate any chosen reaction in a manner similar to that in which nucleic acid ligands can be identified for any given target. In theory, within a candidate mixture of approximately $10^{13}$ to $10^{18}$ nucleic acids, the present inventors postulate that at least one nucleic acid exists with the appropriate shape to facilitate a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned, describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443,957, now U.S. Pat. No. 5,580,737, describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXPONENTIAL Enrichment: Solution SELEX," abandoned in favor of U.S. patent application Ser. No. 08/461,069, now U.S. Pat. No. 5,567,588, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by EXponential Enrichment: Chimeric SELEX", now U.S. Pat. No. 5,637,459, and U.S. patent application Ser. No. 08/234,997, filed Apr. 28, 1994, entitled "Systematic Evolution of Ligands by EXponential Enrichment: Blended SELEX," now U.S. Pat. No. 5,683,867 respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Previous efforts have demonstrated the use of SELEX to identify ligands that can act facilitatively. In co-pending application, International Publication No. WO 95/08003, filed Sep. 16, 1994 which is a Continuation in Part of U.S. patent application Ser. No. 08/123,935, filed Sep. 17, 1993, entitled "Photoselection of Nucleic Acid Ligands," specifically incorporated by reference, certain nucleic acid sequences that contained 5-iodouracil residues were identified that covalently bind to HIV-1 Rev protein. In co-pending patent application U.S. application Ser. No. 08/234,997, filed Apr. 28, 1994, entitled "Systematic Evolution of Ligands by Exponential Enrichment: Blended SELEX," now U.S. Pat. No. 5,683,867, specifically incorporated by reference, a nucleic acid ligand to human neutrophil elastase was identified wherein a functional unit was associated with the nucleic acid ligand. In this instance, the functional unit was a valyl phosphonate that bound covalently to the elastase target. In co-pending patent application U.S. application Ser. No. 08/309,245, filed Sep. 20, 1994, entitled "Parallel SELEX," now U.S. Pat. No. 5,723,289, specifically incorporated herein by reference, the covalent reaction between a pool of reactants to form a product library is specifically facilitated by a nucleic acid attached to certain reactants.

Ribonucleic acid (RNA) is a biopolymer that is integral to protein synthesis and cellular metabolism. RNA is primarily composed of four basic monomers interlinked with phosphate diester linkages to form a directional (5'-3') polymer. In nature RNA molecules are usually transcribed as single stranded and may fold in various lengths and shapes, ranging from short oligoribonucleotide primers for DNA synthesis to the very large ribosomal RNAs which form part of the translational machinery active during protein synthesis. The purine and pyrimidine bases of RNA interact via ring-stacking and hydrogen bonding networks to fold the polymer chains into compact structures containing surfaces capable of providing specific binding sites for a variety of ligands, including proteins, nucleic acids, divalent metal ions, and carbohydrates (Saenger (1984) in *Principles of Nucleic Acid Structure* (C. R. Cantor, ed.) Chapters 6, 8, and 10, Spinger-Verlag, New York, N.Y.). Single stranded RNA (ssRNA) molecules commonly form localized regions of secondary structure, such as hairpin loops and pseudoknot structures, by base-pairing between complementary regions of the same molecule. (Schimmel (1989) Cell 58:9). The 2'-hydroxyl group provides additional hydrogen bonding capacity and serves as a modest nucleophile in the presence of electropositive magnesium ions. In fact, some RNAs are capable of topologically juxtaposing surface recognition and catalysis elements to promote metal co-factor driven chemical reactions such as transesterification and phosphodiester bond hydrolysis (Cech (1987) Science 236:1532–1539). These sophisticated attributes have prompted investigators to pursue therapeutic applications based on RNA catalysis and specific ligand binding activities.

Studies to date have identified only a few nucleic acids which have only a narrow subset of facilitating capabilities. A few RNA catalysts are known (Cech (1987) Science 236:1532–1539; McCorkle and Altman (1987) Journal of Chemical Education 64:221–226). These naturally occurring RNA enzymes (ribozymes) have to date been shown to act primarily on oligonucleotide substrates. Further, these molecules perform over a narrow range of chemical possibilities, which are thus far related primarily to phosphodiester bond condensation/hydrolysis, with the exception of the possible involvement of RNA in protein biosynthesis. Despite intense recent investigation to identify RNA or DNA catalysts, few successes have been identified. Phosphodiester cleavage (Beaudry and Joyce (1992) Science 257:635), hydrolysis of aminoacyl esters (Piccirilli et al. (1992) Science 256:1420–1424); self-cleavage (Pan and Uhlenbeck (1992) Biochemistry 31:3887), RNA polymerase activity (an RNA polymerase is an enzyme which facilitates the ligation of the 3' OH of one RNA molecule with the 5' triphosphate end of a second RNA molecule) (Bartel and Szostak (1993) Science 261:1411–1418); biphenyl isomerase activity (Prudent et al. (1994) Science 264:1924–1927); and polynucleotide kinase activity (a kinase is an enzyme which facilitates the transfer of a phosphate from one substrate to another) (Lorsch and Szostak (1994) Nature 371:31–36) have been observed. Dai et al. (1995) Science 267:237–240, have identified an RNA ligand which facilitates the cleavage of an alkyl amide.

The nucleic acid catalysts identified to date have certain shortcomings associated with their effectiveness in bond forming/breaking reactions. Among the drawbacks are that they act slowly relative to protein enzymes, and as described above, they perform over a somewhat narrow range of chemical possibilities.

Transfer RNA (tRNA) is a type of RNA molecule which acts as an adaptor during protein synthesis, matching amino acids (aa) to their codons on messenger RNA (mRNA). Before an amino acid is incorporated into a protein chain, it is attached by its carboxyl end to the 3' end of a tRNA molecule. This reaction is facilitated in two steps by a class of enzymes referred to as aminoacyl-tRNA synthetases, as illustrated in equations (1) and (2). In the first step, equation (1), aminoacyl-tRNA synthetase activates the carbonyl group of the amino acid (aa) by forming the aminoacyl-adenylate, in which the carboxyl group of the amino acid is attached to adenosine monophosphate (AMP):

(1)

(2)

A tRNA molecule carrying its cognate amino acid is said to be "charged". The enzyme bound adenylate therefore, facilitates the esterification of the 2'(3') hydroxy terminus of transfer RNA, to create an aminoacyl-tRNA molecule.

SUMMARY OF THE INVENTION

The present invention includes methods for selecting and identifying nucleic acid ligands and the nucleic acid ligands so identified and produced. Specifically, the present invention includes a method for selecting and identifying nucleic acid ligands from a candidate mixture of randomized nucleic acid sequences on the basis of the ability of the randomized nucleic acid sequences to facilitate aminoacyl-RNA synthesis.

In one embodiment, the method comprises preparing a candidate mixture of nucleic acid sequences; contacting the candidate mixture with an aminoacyl-nucleoside monophosphate mixed anhydride reactant molecule, particularly aminoacyl-adenylate (aa-AMP), wherein nucleic acid sequences having facilitative activity are able to facilitate or enhance a reaction between the aa-AMP reactant molecule and nucleic acid sequence, thereby forming an aminoacyl-RNA, partitioning the product of the reaction between the nucleic acid ligand and the reactant from the free nucleic acids in the candidate mixture; and identifying the nucleic acid sequences that were able to facilitate the reaction. The process can further include the iterative step of amplifying the nucleic acids that facilitated the reaction to yield a mixture of nucleic acids enriched in sequences that are able to facilitate a particular chemical reaction.

In another embodiment of the invention nucleic acid sequences are provided that are capable of facilitating aminoacyl-RNA synthesis. Specifically, RNA sequences are provided that are capable of facilitating or enhancing aminoacyl-RNA synthesis. Included within the invention are the nucleic acid ligand sequences capable of facilitating or enhancing aminoacyl-RNA synthesis.

The nucleic acids of the present invention include single- and double-stranded RNA and single- and double-stranded DNA. The nucleic acids of the present invention may contain modified groups such as 2'-amino (2'-$NH_2$) or 2'-fluoro (2'-F)-modified nucleotides. The nucleic acids of the present invention may further include backbone modifications.

Further included in the present invention is a method for treating diseases caused by a deficiency of aminoacyl-transferase by the administration of the ligands described herein. Specifically, the present invention includes a nucleic acid ligand capable of stabilizing a similar transition state for any biosynthesis which is carried out by a nucleic acid performing a similar reaction.

The present disclosure provides non-limiting examples which are illustrative and exemplary of the invention.

DETAILED DESCRIPTION OF INVENTION

The present invention is a variation of the SELEX method for selecting nucleic acid ligands. This application hereby specifically incorporates by reference the full text including the definitions provided in the earlier SELEX patent applications, specifically those provided in U.S. patent application Ser. No. 07/536,428, entitled "Systematic Evolution of Ligands by EXponential Enrichment," now abandoned, U.S. patent application Ser. No. 07/714,131, filed Jun. 10, 1991, entitled "Nucleic Acid Ligands," now U.S. Pat. No. 5,475,096, and U.S. patent application Ser. No. 07/931,473, filed Aug. 17, 1992, entitled "Methods for Identifying Nucleic Acid Ligands," now U.S. Pat. No. 5,270,163, (see also WO 91/19813). The present invention identifies and selects nucleic acid ligands capable of facilitating or enhancing aminoacyl-RNA synthesis.

The present invention encompasses nucleic acid ligands which are single- or double-stranded RNA or DNA oligonucleotides. The nucleic acid ligands of the present invention are capable of facilitating or enhancing aminoacyl-RNA synthesis when combined with aminoacyl-nucleoside monophosphate mixed anhydride, particularly an aminoacyl-adenylate under conditions conducive to reaction. Further, the present invention encompasses nucleic acid ligands containing any modification thereof. Such modifications include, but are not limited to, modifications at cytosine exocyclic amines, substitution with halogenated groups, e.g., 5'-bromo- or 5'-iodo-uracil, modification at the 2'-position, e.g., 2'-amino (2'-$NH_2$) and 2'-fluoro (2'-F), backbone modifications, methylations, unusual base-pairing combinations and the like. For example, the nucleic acid ligands of the present invention may include modified nucleotides such as 2'-$NH_2$-iodouracil, 2'-$NH_2$-iodocytosine, 2'-$NH_2$-iodoadenine, 2'-$NH_2$-bromouracil, 2'-$NH_2$-bromocytosine, and 2'-$NH_2$-bromoadenine.

Certain terms are used to describe the invention herein are defined as follows:

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the individual nucleic acid bases or to the nucleic acid as a whole. Such modifications include, but are not limited to, modified bases such as 2'-position base modifications, 5-position pyrimidine modifications, 8-position purine modifications, 7-position purine modifications, modifications at cytosine exocyclic amines, substitution of 5-bromo-uracil; backbone modifications, methylations, unusual base-pairing combinations such as the isobases isocytidine and isoguanidine and the like. Modifications can also include 3' and 5' modifications such as capping. Modifications that occur after each round of amplification are also compatible with this invention. Post-amplification modifications can be reversibly or irreversibly added after each round of amplification. Virtually any modification of the nucleic acid is contemplated by this invention. The length of the randomized section of the nucleic acid is generally between 8 and 500 nucleotides, preferably between 8 and 60 nucleotides.

"Nucleic acid candidate mixture" is a mixture of nucleic acids of differing, randomized sequence including some which have a shape which enables them to mediate the formation and/or cleavage of chemical bonds. The source of a "nucleic acid candidate mixture" can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic acid having facilitative properties" or "facilitative nucleic acid" or "nucleic acid" refers to any nucleic acid which is capable of facilitating the reaction between an RNA ligand and an aminoacyl nucleoside monophosphate mixed anhydride, particularly aminoacyl-adenylate to form an aminoacyl-RNA. The rate of the chemical reaction is increased or enhanced by the presence of the facilitative nucleic acid. The facilitative nucleic acid can mediate the chemical reaction either alone, or in combination with another facilitative moiety which could be found in solution. The other facilitative moieties can include metal ions, buffer ions and other reaction components.

"Reactant" refers to any chemical entity that could be involved in a bond forming or bond cleavage reaction which is compatible with the thermal and chemical stability of nucleic acids. Preferred reactants are aminoacyl nucleoside monophosphate mixed anhydrides. The nucleoside monophosphate mixed anhydride can be a natural or modified nucleoside monophosphate. The aminoacyl group can be any natural or non-naturally occurring amino acid and may include a peptide of up to about 10 amino acid units wherein the terminal amino acid is activated to form aminoacyl mixed anhydride. In one embodiment of the present invention the reactant is an aminoacyl-adenylate (aa-AMP), in which the carboxyl group of the amino acid is attached to adenosine monophosphate (AMP). As one example, the amino acid is phenylalanine.

"Product" refers to a compound resulting from a bond forming reaction which has been facilitated by a nucleic acid. In a preferred embodiment, a product is formed between the reactant and the facilitative nucleic acid.

"Partitioning" means any process whereby members of the nucleic acid candidate mixture or nucleic acid-reactant candidate mixture can be separated from the bulk of the candidate mixture based on the ability of the nucleic acid to facilitate a reaction involving its associated reactant, resulting in a desirable product. Partitioning can be accomplished by various methods known in the art. Filter binding, affinity chromatography, liquid-liquid partitioning, filtration, gel shift, density gradient centrifugation are all examples of suitable partitioning methods. The choice of partitioning method will depend on properties of the target and the product and can be made according to principles and properties known to those of ordinary skill in the art.

"Amplifying" means any process or combination of process steps that increases the amount or number of copies of a molecule or class of molecules. In preferred embodiments, amplification occurs after members of the candidate mixture have been partitioned, and it is the facilitative nucleic acid associated with the desirable product that is amplified. For example, amplifying RNA molecules can be carried out by a sequence of three reactions: making cDNA copies of selected RNA's, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the mixture prior to amplification. It is known that many modifications to nucleic acids are compatible with enzymatic amplification. Modifications that are not compatible with amplification can be made after each round of amplification, if necessary.

"Randomized" is a term used to describe a segment of a nucleic acid having, in principle, any possible sequence over a given length. Randomized sequences will be of various lengths, as desired, ranging from one to more than five hundred nucleotides. The chemical or enzymatic reactions by which random sequence segments are made may not yield mathematically random sequences due to unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into a randomized sequence, for example, by altering the molar ratios of precursor nucleoside (or deoxynucleoside) triphosphates in the synthesis reaction. A deliberate bias may be desired, for example, to affect secondary structure, to introduce bias toward molecules know to have facilitating activity, to introduce certain structural characteristics, or based on preliminary results.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to select and amplify nucleic acids having facilitative properties.

In one embodiment of the present invention a randomized set of nucleic acid sequences, termed the candidate mixture, is mixed with a reactant under conditions conducive to reaction between facilitative nucleic acid ligands and the reactant and the reaction is allowed to proceed.

As stated above, the candidate mixture is comprised of regions of fixed sequences (i.e., each of the members of the candidate mixture contains the same sequences in the same location) and regions of randomized sequences. The fixed sequence regions are necessary for efficient amplification. The randomized sequences can be totally randomized (i.e., the probability of finding a base at any position being one in four) or only partially randomized (e.g., the probability of finding a base at any location can be selected at any level between 0 and 100 percent).

The reactant molecule can comprise any aminoacyl nucleoside monophosphate mixed anhydride. Preferred reactants include any amino acid, specifically phenylalanine (Phe), alanine (Ala) and serine (Ser) coupled to any nucleoside monophosphate. In one embodiment the reactant is an aminoacyl-adenylate (aa-AMP) and the reaction being facilitated is the aminoacylation of RNA (Equation 2). In a preferred embodiment the amino acid is phenylalanine. In another embodiment, the acyl group can be an imidazole and the reactant an imidazole AMP.

Following reaction, the nucleic acids which have reacted with the reactant to form aminoacyl-RNAs are partitioned from the remainder of the nucleic acid mixture. Because only an extremely small number of sequences (and possibly only one molecule of nucleic acid) corresponding to the nucleic acids most capable of facilitating a specific reaction exist in the candidate mixture, it is generally desirable to set the partitioning criteria so that a significant amount of the nucleic acids in the candidate mixture (approximately 0.005–50%, preferably 0.1–10%) are retained during partitioning. In one embodiment of the present invention, the aminoacyl-RNAs are derivatized with a hydrophobic group and are then partitioned from the remainder of the reaction mixture by high pressure liquid chromatography. The hydrophobic group is selected from the group consisting of any hydrophobic group with an attached acyl moiety. In a preferred embodiment the hydrophobic group is a naphthoxyacetyl-NHS group.

Those nucleic acids selected during partitioning are then amplified to create a new candidate mixture that is enriched in nucleic acids capable of facilitating the specific reaction. The process of selection, partitioning and amplification can then be repeated.

The method of the present invention is illustrated by the selection and identification of RNA ligands capable of facilitating aminoacyl-RNA synthesis (Equation (3)):

$$\text{aa-NMP} + \text{RNA} \rightarrow \text{aa-RNA} + \text{NMP} \tag{3}$$

In this invention wherein aaNMP represents a mixed anhydride between any nucleoside monophosphate and any amino acid moiety, including activated peptides of up to about 10 amino acids, RNA ligands are selected and identified that are capable of facilitating or enhancing the aminoacylation of RNA. As stated above, in biological systems one example of this reaction is facilitated by a class of enzymes referred to as aminoacyl-tRNA synthetases. The reaction requires both $Ca^{2+}$ and $Mg^{2+}$ in the range generally of 1–50 nM. In a preferred embodiment the amino acid is phenylalanine.

Example 1 describes the synthesis of phenylalanyl-AMP (Phe-AMP). This compound was synthesized using a procedure reported by Berg (1958) J. Biol. Chem. 233:608. Because of slow aminoacyl migration from the 5'-phosphate of AMP to its 2' and 3' hydroxyls (Wickramasinghe et al. (1991) Biochemistry 30:2768), the adenylate is contaminated with small amounts of 2'(3')-O-aminoacyl esters of AMP, a potential alternative form of activated amino acid. However, controls in which the unstable adenylate was quickly hydrolyzed before introduction of the RNA, leaving the more stable ribose esters of AMP, do not give the reactions below. Thus the source of the Phe group in what follows was the adenylate, Phe-AMP, not the minor but inevitable 2'(3')-O-aminoacyl esters.

Example 2 describes the reaction conditions for the reaction of the random pool of RNA with Phe-AMP. Briefly, Phe-AMP is added to a pool of randomized RNA sequences [50 contiguous randomized nucleotides; $1.7 \times 10^{14}$ distinct initial sequences], under conditions conducive to aminoacyl-transfer. In the preferred embodiment the reaction is run at pH 7 and 0° C., in the presence of moderate concentrations of $Na^+$, $K^+$, $Ca^{2+}$ and $Mg^{2+}$. Reaction components are otherwise unexceptional, except for inclusion of divalent metal cations, such as $Ca^{2+}$, $Mn^{2+}$ and $Zn^{2+}$ during selection. $Cu^{2+}$ is added to provide for possible utilization in an RNA structure. (Brown and Bugg (1980) Acta. Crystallogr. B36:2597). The final product only required $Ca^{2+}$, $Mg^{2+}$ and $Mn^{2+}$.

Figure 1:
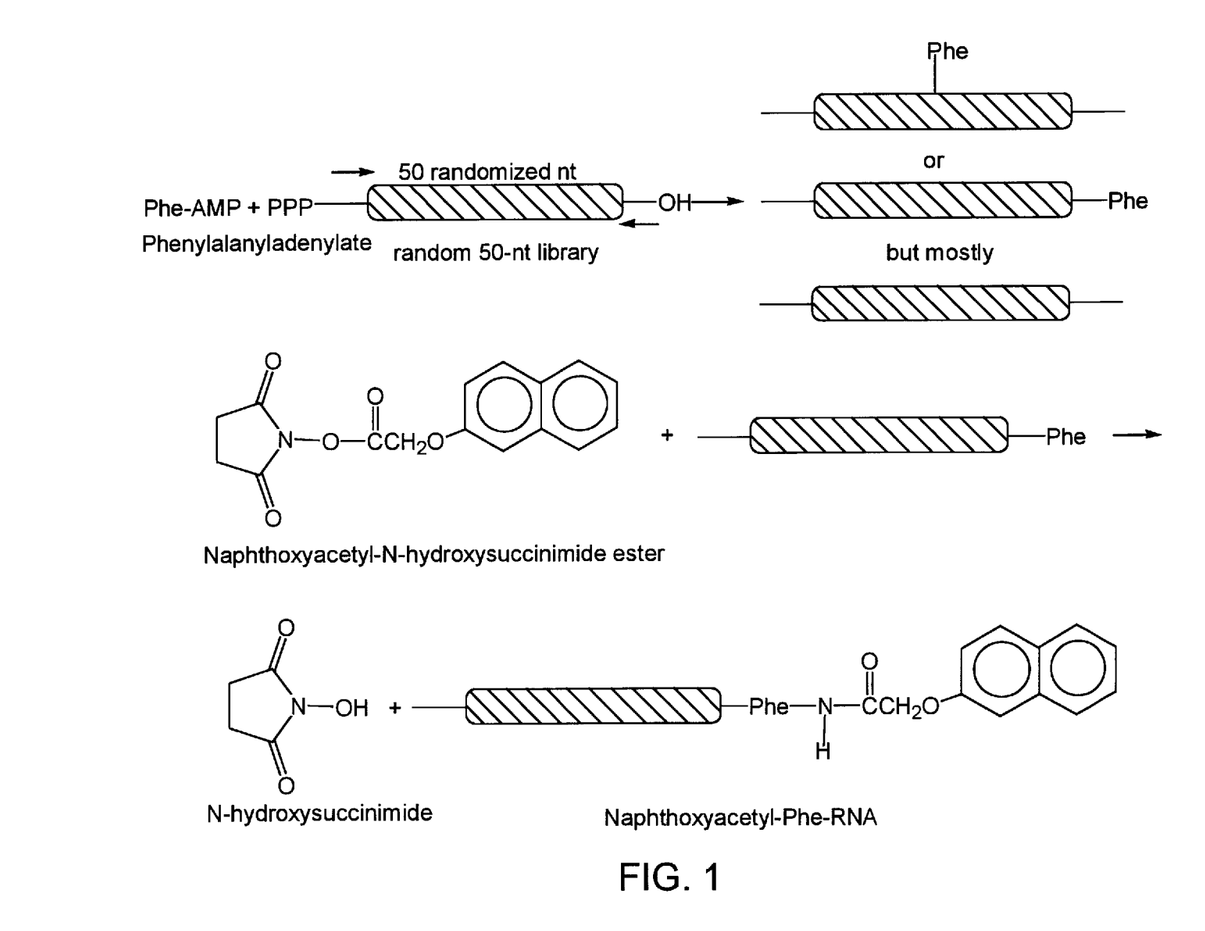
FIG. 1 depicts facilitative RNA selection by product trapping.

Referring to FIG. 1, following reaction three types of RNA ligands are present in the mixture: (A) RNA ligands in which the aminoacyl group has been transferred to an internal nucleotide; (B) RNA ligands in which the aminoacyl group has been transferred to the 3'-terminal nucleotide (the desired product, Phe-RNA) referred to herein as the "aminoacyl-RNA"); and (C) RNA ligands that have not reacted.

When the incubation is complete, the reaction mixture is treated with naphthoxyacetyl-N-hydroxysuccinimide ester (naphthoxyacetyl-NHS ester). The α-amino group of the Phe-RNA reacts with the naphthoxyacetyl-NHS ester to provide naphthoxyacetyl-Phe-RNA, which enables separation or partitioning of the desired product from the remainder of the reaction mixture by high pressure liquid chromatography (HPLC) and also stabilizes the product to hydrolysis.

The derivatized naphthoxyacetyl-Phe-RNAs were resolved by means of a chromatographic system that responds strongly to addition of a large hydrophobic group to a macromolecular RNA. RNA ligands cannot be resolved by HPLC on porous $C_4$-glass columns (retention time, about 14.5 minutes). The addition of a mildly hydrophobic group, such as, the Phe- group of the Phe-RNA, does not increase the ability to resolve the product of the reaction from the unreacted RNA ligands, as exemplified by the position of Phe-tRNA$^{Phe}$ (yeast). However, when Phe-RNA was derivatized with naphthoxyacetyl-, the RNA (exemplified by naphthoxyacetyl-Phe-tRNA$^{Phe}$) eluted much later, having retention times similar to small hydrophobic molecules like naphthoxyacetate and its NHS ester.

The naphthoxyacetyl-Phe-RNA was subjected to the SELEX process, as described in the SELEX patent applications, through 11 cycles of exposure to Phe-AMP and naphthoxyacetylation. Internal 2'-aminoacyl linkages hydrolyze under these conditions.

After 11 cycles the RNA ligands isolated were converted to cDNA, cloned and sequenced by dideoxynucleotide extension (Tuerk and Gold (1990) Science 249:505) and 42 sequences were identified. Of the 42 sequences, 35 were each different from the other, 3 were a set of identical sequences and 4 comprised sets of two. The identified nucleic acid ligands are represented by SEQ ID NOS:2–10 (Table 1).

Figure 4:
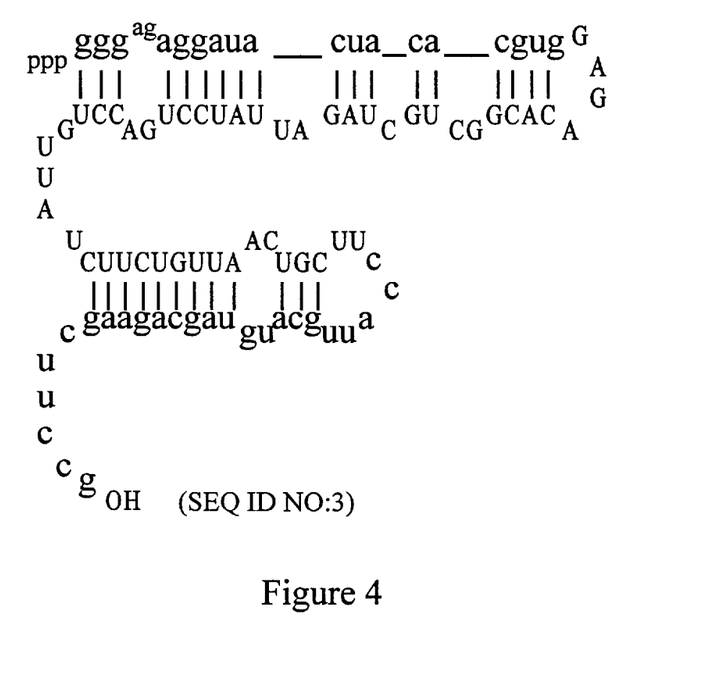
FIG. 4 depicts isolate 29 RNA (SEQ ID NO:3) in its most stable secondary structure, determined by Mfold (Zucker (1989) Science 244:48–52) and confirmed by chemical probing. Lowercase letters represent fixed nucleotides complementary to the PCR primers and uppercase letters represent nucleotides originally randomized.

One in five clones, transcribed and tested individually by HPLC, was highly reactive with Phe-AMP. One sequence, isolate 29 (SEQ ID NO:3), is shown in FIG. 4. As can be seen in FIG. 4, the calculated stable secondary structure of isolate 29 shows two hairpin domains with small bulge and loop defects. This distribution of loops, bulges and helices is in excellent agreement with the RNA's kethoxal and lead susceptibilities; therefore the calculated secondary structure is realistic. The 3' domain that bears the amino acid resembles the Tψ-CCA domain of a tRNA in some respects. But this sequence represents a single parent; accordingly, the relative importance of isolate $_{29}$'s substructures is not deductible from the original selection.

The product of the reaction of phenylalanyl-adenylate and isolate 29 RNA was verified by various chemical means. For example, the initial reaction product had the buffer sensitivity characteristic of aminoacyl esters of ribose (Gottikh et al. (1970) Tetrahedron 28:4419), that is mild alkaline hydrolysis after exposure to Phe-AMP (37° C. for 1 hour, 0.2M tris-HCl, pH 8) prevented appearance of the reaction product.

Additionally, the initial product appeared to be subsequently converted to N-blocked aminoacyl-RNA, as intended (FIG. 1), in that exposure to $Cu^{2+}$ after exposure to Phe-AMP prevented formation of the product, but had no effect on the product after reaction with naphthoxyacetyl-NHS (See Example 4). This corresponds to the sensitivity of aa-RNA to $Cu^{2+}$-facilitated hydrolysis, and the expected resistance to the same treatment once the α-amino group is blocked. Formation of the product required the guanosine terminal 2'(3') ribose hydroxyls. Periodate oxidation of the ligands prior to exposure to Phe-AMP prevents product formation, whereas the same oxidation has no effect after exposure to Phe-AMP (Example 5). Thus, the 2'(3') cis-diol of the terminal ribose, which is oxidized very specifically by periodate, is required for formation of the chromatographically detected product. Once acylated, the 2'(3') terminus would be blocked and resistant to subsequent periodate oxidation, as was observed. Thus, isolate 29 aminoacyl-RNA bore the aminoacyl at its 3' terminus, as would an aminoacyl-tRNA.

Figure 2:
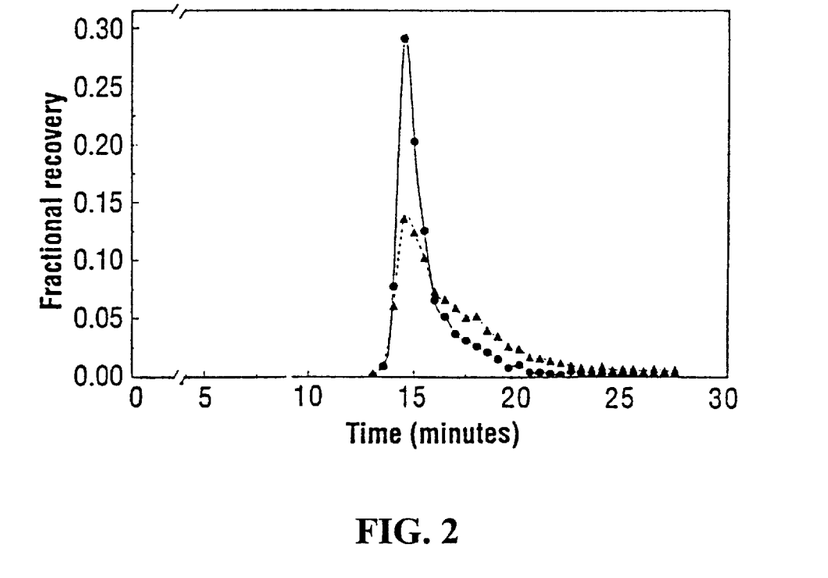
FIG. 2 depicts the chromatography and rechromatography of RNA in the randomized initial pool (solid lines and circles) and the fractionation of RNA reacted with Phe-AMP followed by naphthoxyacetyl-NHS (dotted lines and triangles), the refractionation of RNA eluting at 17.5 to 25 minutes.
Figure 3:
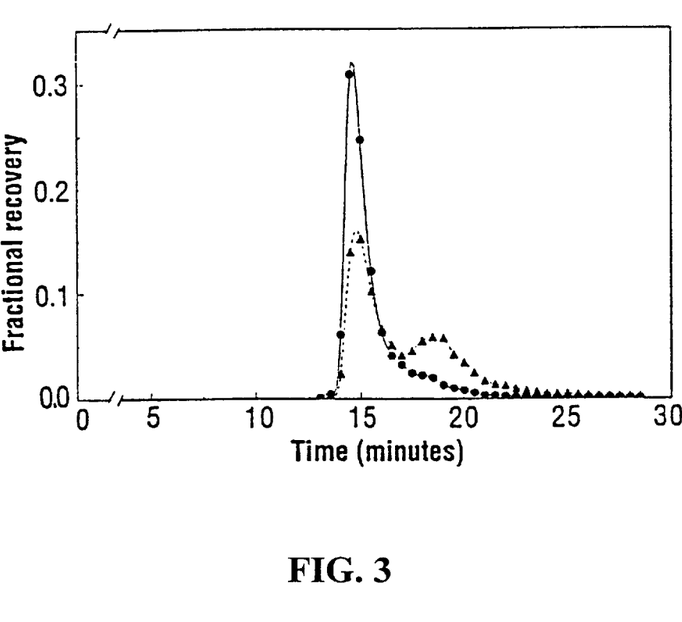
FIG. 3 depicts the chromatography and rechromatography of RNA at cycle 11 of selection (solid lines and circles), and the fractionation of RNA reacted with Phe-AMP, followed by naphthoxyacetyl-NHS (dotted lines and triangles), refractionation of RNA eluting at 17.5 to 25 minutes.

Kinetic studies have shown that aminoacylation of isolate 29 RNA is highly accelerated. Using the double HPLC criterion of FIGS. 2 and 3, no acylation of the initial pool was detected. That is, controls (for example, without adenylate) were virtually indistinguishable from the full reaction shown in FIG. 2. Estimating an upper limit for a hypothetical hydrophobic (trailing) peak, it is calculated that after 2 hours at 0° C. at an initial concentration of 11 mM Phe-AMP, $\leq 1.3 \times 10^{-3}$ of random RNA has reacted.

$$k_{random} = \frac{\text{fraction - reacted}}{\text{time[Phe - AMP]}} \leq 1.0 \times 10^{-3} M^{-1} \text{min}^{-1}$$

The background rate is estimated as a second-order rate constant because isolate 29's reaction is approximately first order in both RNA and adenylate under our conditions. Lability of the adenylate and the ester product have been neglected. This slow rate is also consistent with previous experiments (Weber and Lacey (1975) J. Mol. Evol. 6:309), showing that poly(U) and poly(A) are unreactive with Phe-AMP.

By comparison, a 50 percent reaction of isolate 29 RNA in 2 minutes at 0° C. with 2 mM Phe-AMP is observed giving a second order rate constant of $\sim 10^2$ $M^{-1}$ $min^{-1}$. Thus, the isolate 29 RNA reaction was approximately 100,000 times or more accelerated. Therefore, an RNA ligand has been identified that facilitates the aminoacyl group transfer reaction which comprises the second step of the reaction facilitated by aminoacyl-tRNA synthetases. The RNA ligand is a good facilitator, in the sense that it rapidly becomes acylated under "ordinary" conditions and concentrations of components.

The following examples are provided for illustrative purposes only and are not intended to limit the scope of the invention.

EXAMPLE 1

Preparation of Phenylalanyl-adenine monophosphate (Phe-AMP)

Phenylalanyl-AMP was synthesized using a modified procedure of Berg (1958) J. Biol. Chem. 233:608. The modification involves the final chromatographic purification, which was necessitated by larger scale synthesis. Briefly, [$^3$H]Phe (2.75 mCi, Amersham (Arlington Heights, Ill.); 124 Ci/mmol) was dried at reduced pressure and combined with 15 μmol of nonisotopic L-phe and 15 μmol of 5'-AMP (Sigma) and dissolved in 7 μl of $H_2O$. (The tritium labeled compound is only used when the reaction is being run to verify structure.). This mixture was cooled to 0° C., followed by the addition of pyridine (79 μl) and HCl (19 μl of 0.8N). Dicyclohexylcarbodiimide (DCC) (0.38 mmol) in 86 μl of pyridine was then added with stirring over ice for 3 hours. After 3 hours the product was precipitated with two volumes of acetone at −20° C. and collected by centrifugation. The solids were rinsed with a mixture of acetone and ethanol (60:40) and then ether, dissolved in 400 μl of $H_2O$ at 0° C. and absorbed onto a Sep-Pak $C_{18}$ column (Waters 51910), that had been washed with acetonitrile and $H_2O$.

The absorbed adenylate was washed with 15 ml of water, followed by elution with 1 ml of absolute methanol. The liquid was removed by evaporation at reduced pressure and the material was stored at approximately 70° C. under argon.

An HPLC spectra of purified phenylalanyl-adenine monophosphate (Phe-AMP) was performed in water. An HPLC of the product was run on a $C_4$ porous glass column and eluted with a gradient of acetonitrile and 0.1M ammonium acetate (pH 4.5). Phe-AMP elutes in approximately 22% acetonitrile at 23° C. The spectra showed minor impurities.

EXAMPLE 2

Synthesis of RNA Sequences

An initial RNA pool was prepared by in vitro transcription from synthetic DNA template 5'-CGG AAG CTT CTG CTA CAT GCA ATG G-$N_{50}$-CAC GTG TAG TAT CCT CTC CCT ATA GTG AGT CGT ATT AGA ATT CGC-3' (SEQ ID NO: 1) using T7 RNA polymerase, as described by Milligan and co-workers (Milligan et al. (1987) Nucleic Acids Res. 15:8783). N represents equimolar nucleotides. For renaturation, $4.7 \times 10^{14}$ molecules of gel-purified 95-nucleotide (nt) transcript RNA from $1.7 \times 10^{14}$ independently synthesized DNA templates having a central tract of 50 randomized positions were heated at 65° C. in 20 μl of 1 mM $Mg^{2+}$ for 3 minutes, then quenched in ice.

Selections for facilitative RNA ligands were done by incubation of a mixture of 100 mM Hepes (final pH about 7), 20 mM potassium acetate (KOAc), 200 mM NaCl, 5 mM $CaCl_2$, 10 μM $CuSO_4$, 2 μM $FeCl_3$, 10 mM $MgCl_2$, 100 μM $MnCl_2$ and 5 μM $ZnCl_2$ in a final volume of 50 μl, with 6 to 8 mM Phe-AMP present initially. The mixture was allowed to incubate for 30 minutes on ice, followed by an additional 15 minutes at room temperature. The reaction was quenched by the addition of sodium acetate (pH 5.2) to 300 mM in 150 μl, followed by two volumes of ethanol. The mixture was then centrifuged.

The $Cu^{2+}$ is added to the acylation reaction mixture to provide for possible utilization in an RNA structure (Brown and Bugg (1980) Acta. Crystallogr. B36:2597). The amount added is far below that used to hydrolyze aminoacyl-RNA (Schofield and Zamecnik (1968) Biochim. Biophys. Acta. 155:410).

For purposes of verification of structure the reaction was run as described above, except that $MgCl_2$ (10 mM) and $CaCl_2$(5 nM) were the only divalent metals added. Additionally, 2 mM initial Phe-AMP, 100 μM EDTA, and 0.5 to 2 μg of gel-purified isolate 29 RNA were incubated at 0° C. Products were characterized when about 50 percent of the RNA appeared acylated as determined by HPLC.

EXAMPLE 3

Preparation of the Naphthoxyacetyl-NHS Derivatives

The derivatized product was prepared using a modified procedure of Gillam et al. (1968) Biochemistry 7:3459. Briefly, the centrifuged reaction mixture, containing Phe-RNA was redissolved in 100 μl of 100 mM tris-HCl (pH 8) and 70 percent (v/v) dimethyl sulfoxide (DMSO), containing 250 mM naphthoxyacetyl-NHS ester (Sigma). After 10 minutes at 25° C. the volume of the mixture was increased to 300 μl with sodium acetate (pH 5.2) to a final concentration of 300 mM, 70 percent DMSO. Three volumes of ethanol was added and the precipitate was collected by centrifugation.

The centrifuged RNA products were redissolved in 200 μl of 100 mM ammonium acetate (pH 4.5) containing 50 percent (v/v) DMSO. This material was filtered and purified by high pressure liquid chromatography (HPLC) using a two-pump Waters chromatograph with a 481 absorbance monitor and an electronic gradient controller, containing a $C_4$ porous glass column (Ranin Dynamax-300A; 4.6×250 mm). The mixture was eluted for 2 minutes with 100 mM ammonium acetate (pH 4.5), followed by a one hour Exponential gradient (Waters profile 3) at 1 ml/min consisting of 100 percent 100 mM ammonium acetate (pH 4.5) to 52 percent ammonium acetate and 48 percent acetonitrile (Mallinckrodt HPLC grade). Underivatized RNA elutes in about 31 percent acetonitrile at 23° C. The derivatized RNA was pooled and amplified by complementary DNA (cDNA) synthesis and the polymerase chain reaction (PCR) through 11 cycles of exposure to Phe-AMP and naphthoxyacetylation. (Tuerk and Gold (1990) Science 249:505). Reverse transcription occurs at pH 8.3 and 37° C. in 60 minutes.

EXAMPLE 4

Hydrolysis of Aminoacyl-RNA

Hydrolysis reactions were performed according to the method of Schofield and Zamecnik (1968) Biochem. Biophys. Acta. 55:410. Briefly, 20 mM $CuSO_4$, 50 mM sodium acetate (pH 5.2) and 10 mM $MgCl_2$, were added to the aminoacyl-RNA and the reaction was allowed to proceed for 30 minutes at 23° C. The reaction was quenched with a two fold molar excess of EDTA and the product was precipitated with ethanol prior to chromatography.

EXAMPLE 5

Periodate Oxidations

Periodate oxidations were performed according to the method of Steinschneider and Fraenkel-Conrat (1966) Biochemistry 5:2729. Briefly, 8.2 mM $NaIO_4$, 30 mM sodium acetate (pH 5.2), 60 mM NaCl, and 6 mM $MgCl_2$, was added to the compound to be oxidized and the reaction was allowed to proceed for 120 minutes in the dark at 0° C. Residual periodate was consumed by addition of two fold molar excess of glucose, followed by gel filtration and ethanol precipitation before HPLC fractionation. Periodate oxidation of the ligands prior to exposure to Phe-AMP prevents product formation, whereas the oxidation has no effect after exposure to Phe-AMP.

EXAMPLE 6

Preparation of Phe-2'(3')-O-GMP

For the synthesis of Phe-2'(3')-O-GMP, a modification of the procedure of Example 1 was used as described by Gottikh, et al (1970) Tetrahedron 28:4419. Briefly, carbonyldiimidazole (375 μmol) (Sigma) and tBOC-L-phenylalanine (Sigma) were dissolved in dry tetrahydrofuran. After 10 minutes at 23° C., this mixture was added to 20 μmol of disodium 5' GMP in 500 μl of acetonitrile and $H_2O$ (1:4 by vol). After 20 minutes, this mixture was poured into 15 ml of acetone at 20° C. and centrifuged; the solids were dried under vacuum. The phenylalanine was deprotected by dissolving in 500 μl of trifluoroacetic acid (Fluka), and rapidly removing the trifluoroacetic acid at reduced pressure. The deprotected product was first purified by preparative TLC at 23° C. on cellulose layers (Quantum Industries Q2F), eluting with n-butanol, acetic acid, and $H_2O$ (5:2:3).

An apparently uniform band ($R_f$=0.49) was eluted in water in approximately 16 percent yield. The water-eluted TLC band was resolved into two materials by HPLC on $C_{18}$ glass (Ranin 80-225-C5) in a water-acetonitrile gradient. One (70 percent by $A_{280}$) was the desired product Phe-2'-(3')-O-GMP, which had a spectrum like that of 5'-GMP and was resistant to periodate until treated with mild alkali. The unexpected product (30 percent) was sensitive to periodate and resistant to mild alkali. On the basis of properties and a new absorption peak at 275 nm, the containment may have been aminoacylated at the G base.

TABLE 1

| SEQ ID NO: | |
|---|---|
| 2 | GGGAGAGGAUACUACACGUGUUAAACAACGUUGUAUAGUAAAACACCUGACCUGGUUUCAUUCUGCACUGCCAUUGCAUGUAGCAGAAGCUUCCG |
| 3 | GGGAGAGGAUACUACACGUGGAGACACGGCUGCUAGAUUAUCCUGACCUGUUAUCUUCUGUUAACUGCUUCCAUUGCAUGUAGCAGAAGCUUCCG |
| 4 | CGGAAGCUUCUGCUACAUGCUCAGUCUAAGUUCUCUAAGCGUACUAACACGCUCGUAACAACCCACGCUGCUCCAUUGCAUGUAGCAGAAGCUUCCG |
| 5 | GGGAGAGGAUACUACACGUGUCACCCCCGUCCGAUAACUUCGGCAAACGAUUUCUGCGUACATCAACCACCAUUGCAUGUAGCAGAAGCUUCCG |
| 6 | GGGAGAGGAUACUACACGUGUCCCAUCCAAGACCUCGAUAAAAUCGGUCGACUUGUCUGCGCUGCCCAUUGCAUGUAGCAGAAGCUUCCG |
| 7 | GGGAGAGGAUACUACACGUGGGAAUAAAAAACACUGUCAAACCACUCCAUCACCAAGUUUUCGCUACCCAUUGCAUGUAGCAGAAGCUUCCG |
| 8 | GGGAGAGGAUACUACACGUGUCUAUCACCUGGUCACUGUCUGUUAAUGCAAGUGCGCUUUUUCGAACCAUUGCAUGUAGCAGAAGCUUCCG |
| 9 | GGGAGAGGAUACUACACGUGUCCAAGCAUAACCCUAAUUUUGAAACCUCUGUUACAUUAUCGAAGCCAUUGCAUGUAGCAGAAGCUUCCG |
| 10 | GGGAGAGGAUACUACACGUGUUCAAACCGGUGUGUAAACACAAACACAAAUUUCCGCUAUCCAACUUAAUCUAACCAUUGCAUGUAGCAGAAGCUUCCG |

We claim:

1. A method for identifying nucleic acid ligands which facilitate aminoacyl-RNA synthesis comprising:
   a) preparing a candidate mixture of nucleic acids;
   b) contacting the candidate mixture with an aminoacyl-nucleoside monophosphate mixed anhydride under conditions conducive to aminoacyl-RNA synthesis, wherein nucleic acids which facilitate aminoacyl-RNA synthesis may be partitioned from the remainder of the candidate mixture;
   c) partitioning the nucleic acids having the capability of facilitating aminoacyl-RNA synthesis from the remainder of the candidate mixture; and
   d) amplifying the nucleic acids which facilitate aminoacyl-RNA synthesis to yield a mixture of nucleic acids enriched for sequences which facilitate aminoacyl-RNA synthesis, whereby nucleic acid ligands which facilitate aminoacyl-RNA synthesis may be identified.

2. The method of claim 1 further comprising:
   e) repeating steps b), c) and d).

3. The method of claim 1 wherein said candidate mixture of nucleic acids is comprised of single stranded nucleic acids.

4. The method of claim 3 wherein said candidate mixture of nucleic acids is comprised of single stranded ribonucleic acids.

5. The method of claim 4 wherein said candidate mixture of nucleic acids is comprised of modified RNA.

6. The method of claim 1 wherein said aminoacyl nucleoside monophosphate mixed anhydride comprises an amino acid selected from the group consisting of phenylalanine, alanine and serine.

7. The method of claim 1 wherein said aminoacyl nucleoside monophosphate mixed anhydride comprises an imidazole.

8. The method of claim 1 wherein said aminoacyl-nucleoside monophosphate is an aminoacyl-adenylate.

9. The method of claim 1 further comprising:
   b1) derivatizing said aminoacyl-nucleic acid with a hydrophobic moiety.

10. The method of claim 9 wherein said hydrophobic moiety is a naphthoxyacetyl-N-hydroxysuccinimide group.

11. The method of claim 9 wherein said nucleic acids having the capability of facilitating aminoacyl-RNA synthesis are partitioned by high pressure liquid chromatography.

12. A nucleic acid ligand which facilitates aminoacyl-RNA synthesis identified according to the method of claim 1.

13. A purified and isolated non-naturally occurring nucleic acid ligand which facilitates aminoacyl-RNA synthesis.

14. The purified and isolated non-naturally occurring nucleic acid ligand of claim 13 wherein said ligand is single-stranded.

15. The purified and isolated non-naturally occurring nucleic acid ligand of claim 13 wherein said nucleic acid ligand is RNA.

16. The purified and isolated non-naturally occurring nucleic acid ligand of claim 13 wherein said ligand is selected from the group consisting of the sequences set forth in Table 1, SEQ ID NOS: 2–10.

* * * * *

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
    ( A ) LENGTH: 120 base pairs
    ( B ) TYPE: nucleic acid
    ( C ) STRANDEDNESS: single
    ( D ) TOPOLOGY: linear   ( i i ) MOLECULE TYPE: DNA   ( x i ) SEQUENCE DESCRIPTION: SEQ ID NO: 1:

```
CGGAAGCTTC  TGCTACATGC  AATGGNNNNN  NNNNNNNNNN  NNNNNNNNNN  NNNNNNNNNN        60
NNNNNNNNNN  NNNNCACGT   GTAGTATCCT  CTCCCTATAG  TGAGTCGTAT  TAGAATTCGC       120
```

( 2 ) INFORMATION FOR SEQ ID NO: 2:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear   ( i i ) MOLECULE TYPE: RNA   ( x i ) SEQUENCE DESCRIPTION: SEQ ID NO: 2:

```
GGGAGAGGAU  ACUACACGUG  UUAAACAACG  UUGUAUAGUA  AAACACCUGA  CCUGGUUUCA        60
UUCUGCACUG  CCAUUGCAUG  UAGCAGAAGC  UUCCG                                     95
```

( 2 ) INFORMATION FOR SEQ ID NO: 3:

( i ) SEQUENCE CHARACTERISTICS:
    ( A ) LENGTH: 95 base pairs (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 3:

GGGAGAGGAU ACUACACGUG GAGACACGGC UGCUAGAUUA UCCUGACCUG UUAUCUUCUG 60

UUAACUGCUU CCAUUGCAUG UAGCAGAAGC UUCCG 95

(2) INFORMATION FOR SEQ ID NO: 4:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 4:

CGGAAGCUUC UGCUACAUGC UCAGUCUAAG UUCUCUAAGC GUACUAACAC GCUCGUAACA 60

ACCCACGCUG CUCCAUUGCA UGUAGCAGAA GCUUCCG 97

(2) INFORMATION FOR SEQ ID NO: 5:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 5:

GGGAGAGGAU ACUACACGUG UCACCCCGU CCGAUAACUU CGGCAAACGA UUUCUGCGUA 60

CATCAACCAC CAUUGCAUGU AGCAGAAGCU UCCG 94

(2) INFORMATION FOR SEQ ID NO: 6:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 6:

GGGAGAGGAU ACUACACGUG UCCCAUCCAA GACCUCGAUA AAAUCGGUCG ACUUGUCUGC 60

GCUGCCCAUU GCAUGUAGCA GAAGCUUCCG 90

(2) INFORMATION FOR SEQ ID NO: 7:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 7:

GGGAGAGGAU ACUACACGUG GGAAUAAAAA ACACUGUCAA ACCACUCCAU CACCAAGUUU 60

UCGCUACCCA UUGCAUGUAG CAGAAGCUUC CG 92

(2) INFORMATION FOR SEQ ID NO: 8:

(i) SEQUENCE CHARACTERISTICS:
(A) LENGTH: 91 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO: 8:

| GGGAGAGGAU | ACUACACGUG | UCUAUCACCU | GGUCACUGUC | UGUUAAUGCA | AGUGCGCUUU | 60 |
| UUCGAACCAU | UGCAUGUAGC | AGAAGCUUCC | G | | | 91 |

(2) INFORMATION FOR SEQ ID NO: 9:

(i) SEQUENCE CHARACTERISTICS:
(A) LENGTH: 90 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO: 9:

| GGGAGAGGAU | ACUACACGUG | UCCAAGCAUA | ACCCUAAUUU | UGAAACCUCU | GUUACAUUAU | 60 |
| CGAAGCCAUU | GCAUGUAGCA | GAAGCUUCCG | | | | 90 |

(2) INFORMATION FOR SEQ ID NO: 10:

(i) SEQUENCE CHARACTERISTICS:
(A) LENGTH: 99 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO: 10:

| GGGAGAGGAU | ACUACACGUG | UUCAAACCGG | UGUGUAAACA | CAAACACAAA | UUUCCGCUAU | 60 |
| CCAACUUAAU | CUAACCAUUG | CAUGUAGCAG | AAGCUUCCG | | | 99 |